United States Patent [19]
Blake

[11] Patent Number: 4,795,702
[45] Date of Patent: Jan. 3, 1989

[54] DIAGNOSTIC METHOD FOR GONORRHEA BY ASSAY OF IGA1 FRAGMENTS

[75] Inventor: Milan S. Blake, New York, N.Y.

[73] Assignee: Immunogon Associates, Great Neck, N.Y.

[21] Appl. No.: 826,227

[22] Filed: Feb. 5, 1986

[51] Int. Cl.$^4$ ............................................. G01N 33/53
[52] U.S. Cl. ............................................. 435/7; 435/23; 435/24; 435/34; 435/810; 436/511; 436/513; 436/518; 436/548; 436/804; 436/808; 436/811; 530/387; 935/110
[58] Field of Search ............... 435/7, 810, 23, 34, 435/24; 436/511, 513, 518, 501, 548, 804, 808, 811; 935/110; 530/387

[56] References Cited

U.S. PATENT DOCUMENTS 4,582,699 4/1986 Murray ............................ 436/518

Primary Examiner—Robert J. Warden
Assistant Examiner—Robert Benson
Attorney, Agent, or Firm—Kittie Murray

[57] ABSTRACT

Method for assay of fragments produced by the reaction between the enzyme immunoglobulin A protease and its substrate immunoglobulin A, sub-class 1. IgA1, IgAP and also bacteria which secrete IgAP may be detected. The assay is especially useful in the detection of *Neisseria gonorrhea* and in the diagnosis of gonorrhea.

23 Claims, No Drawings

DIAGNOSTIC METHOD FOR GONORRHEA BY ASSAY OF IGA1 FRAGMENTS

This invention concerns immunoassay of the fragments produced by the enzyme immunoglobulin A protease (IgAP) in the reaction with its substrate immunoglobulin A, sub-class 1 (IgA1). IgA1, IgAP and also bacteria which secrete IgAP may be detected. The assay is especially useful in the detection of *Neisseria gonorrhea* and in the diagnosis of gonorrhea.

BACKGROUND OF THE INVENTION

IgAP has been the subject of intensive study since its discovery in the human body. It has been found that IgAP is secreted by pathogenic bacteria. The enzyme has been implicated in the diseases caused by these bacteria, namely gonorrhea, meningitis and influenza. The substrate of IgAP is IgA1. IgAP hydrolyzes IgA1 at a highly specific site that differs with the bacterial source of enzyme. IgA1 is naturally secreted in the human body by urogenital membranes. It has been observed that the amount of IgA1 on these membranes rises in response to infection (Mulks, et al., *J. Infect. Dis.* (1984) 150: 734–44). Although the role of IgAP in pathogenicity is not clear, it has been postulated that this increase in level is a natural defense mechanism of the body to bacteria which secrete IgAP.

The study of IgAP and its reaction with IgA1 would be aided by a rapid, simple assay for the enzyme. Current methods are cumbersome and time-consuming. Immunoelectrophoresis is a sophisticated technique which separates reaction products according to size and charge and then identifies them with anti-sera (Plaut, et al (1974) *Adv. Exp. Med. Biol.*, 45: 245–249; Male C. J. (1979) *Inf. Immun.*, 26: 254–261). SDS-PAGE analysis of 125I-labeled IgA1 is a sensitive technique, but is also time consuming (Blake, et al. (1979) *J. Infect. Dis.*, 139: 89–92; Blake and Swanson (1978) *Inf. Immun.*, 22: 350–358) Lindahl reports an assay utilizing IgA-binding protein from Group A streptococci which is useful under laboratory conditions but this method is also limited by time and labor requirements (Lindahl, L. (1981) *J. Clin. Microbiol.*, 13: 991–993).

Accordingly, a rapid, simple assay of IgAP and its substrate IgA1 has been sought. A simple assay would allow detection of bacteria which secrete the enzyme and make possible early diagnosis of disease.

SUMMARY OF THE INVENTION

The present invention sets forth a method for determining fragments of immunoglobulin A, sub-class 1 (IgA1) produced by the enzymatic digestion of IgA1 by immunoglobulin A protease (IgAP). The method comprises immunoassay of the fragments with antibody which is capable of reacting with the fragments, but not with the undigested IgA1. Preferably, the antibody used in the present assay is monoclonal antibody which is capable of reacting specifically with neo-epitope found on the fragment of IgA1 produced during digestion of IgA1 with IgAP. The neo-epitope is not found on intact IgA1. Immunoassays involving the antibody may comprise enzyme-linked immunoassay, radioimmunoassay, sandwich hybridization or any of the methods well known in the art.

IgA1 may be detected in a sample such as a biological extract by contacting the sample with IgAP under conditions suitable for reaction between IgA1 and IgAP to form fragments of IgA1 and detecting these fragments by the immunoassay of the present invention. IgAP may be detected in a sample by contacting the sample with IgA1 under conditions suitable for reaction to form fragments of IgA1 and measuring these fragments by the immunoassay of the present invention.

Bacteria which secrete the enzyme IgAP may be detected by measuring IgAP by the present method. Among the bacteria which may be so detected are certain species of Neisseria, Haemophilus and Streptococcus. The sample containing bacteria may be cultured prior to assay for IgAP in order to increase the amount of IgAP to be measured and thus to increase the sensitivity of the assay.

The method of the present invention is especially useful in the diagnosis of gonorrhea. Pathogenic studies of *Neisseria gonorrhea*, the causative agent of gonorrhea, secrete IgAP. It has been observed that the IgA1 from urogenital secretions, vaginal wall and urinary tract, which have been exposed to *N. gon.* and thus to IgAP is cleaved in vivo by the enzyme. The fragments so produced may be assayed by the method of the present invention. Preferably, the diagnosis comprises contacting a sample, extract from urogenital tract, throat or rectum, for example, from an individual with a substance capable of binding the Fc portion of IgA1. The substance may be an antibody, preferably a monoclonal antibody specific for the Fc portion or may be the IgA binding protein which is the subject of copending U.S. patent application Ser. No. 446,317. The sample is also contacted either sequentially or at the same time with antibody capable of binding neo-epitope on the fragment. Reaction conditions are maintained to allow bonding of the IgA1 fragment in the sample with both the substance and the antibody. Preferably, either antibody or the substance is labeled with a group that may be observed—a color-forming group such as an enzyme, for example, a radioactive or fluorescent group. Most preferably, either the substance or the antibody is immobilized on an inert support and the bound fragment is thereby removed from the sample. The bound fragment is removed from the sample, is preferably washed and the label on the substance or antibody is measured in either the bound substance or antibody or in the sample.

The present invention also provides reagent for assay of fragments IgA1 produced by enzymatic digestion with IgAP. The reagent comprises antibody capable of reacting specifically with neo-epitope on the fragment produced by enzymatic digestion of IgA1 with IgAP, but it is incapable of reacting with undigested intact IgA1. The reagent is preferably monoclonal antibody produced by immunization of a host animal, a BALB/c mouse, for example, with fragments prepared by digesting IgA1 with IgAP. Monoclonal antibodies which react with the fragment, but not with intact IgA1 are suitable for use as reagent. This reagent may be used to assay IgA1 and IgAP and also the bacteria which produce IgAP and is especially suitable for use in diagnosis of gonorrhea. In this diagnosis, the reagent comprises antibodies which are specific for neo-epitopes formed by digestion of IgA1 and with IgAP *Neisseria gonorrhea*.

Kits for diagnosis of gonorrhea are provided comprising reagent for assay of in vivo fragments of IgA1 produced by reaction with IgAP. The kits may comprise, in addition, means for collection of sample from an individual.

DETAILED DESCRIPTION OF THE INVENTION

In the method of the present invention, fragments of IgA1 are determined by immunoassay with antibody, preferably monoclonal antibody, which reacts specifically with the fragments produced when the enzyme IgAP reacts with IgA1. IgA1 has the following structure:

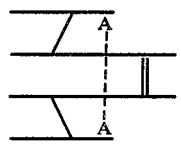

IgAP cleaves IgA1 at the line indicated A—A. The precise location of the cleavage site by IgAP differs with bacterial source of the enzyme. Thus IgAP from *N. gon.* cleaves a threonyl-prolyl bond at the hinge region (residue 235-236), IgAP from *N. meningitides* cleaves IgA1 at pro-ser, bond (residue 237-238) and IgAP from *H. influenza* cleaves IgA1 at a pro-ser bond (residue 231-232). Over 12 different kinds of IgAP, all with IgA1 substrate but with different cleavage sites have been reported (Plaut, Andrew, *Annual Review of Microbiology* (1983), 37: 603–622).

The fragments produced by action of IgAP on IgA1 are generally Fc and Fab fragments, but the neo-epitope comprising amino acids and surrounding carbohydrates exposed by cleavage will differ depending on which bacterial IgAP is used as hydrolytic agent. Highly specific antibodies are capable of recognizing these newly formed epitopes. Moreover, because the neo-epitopes presented by the fragments are not available on intact IgA1, these specific antibodies will not react with intact IgA1. The antibodies may thus be used to distinguish fragments from intact IgA1 and also to distinguish bacterial origin of IgAP used to make the fragments.

Immunoassay of the present invention may be competitive binding assays such as enzyme-linked immunoassay or radioimmunoassay, or may be sandwich assays or any other immunoassay well known in the art.

Generally, the method comprises contacting a sample containing fragments of IgA1 produced during hydrolytic cleavage of IgAP with antibody capable of reacting with the neo-epitopic site on the fragment, this site not being present on intact IgA1. This antibody has the additional property of being incapable of reacting with the intact IgA1 molecule. The antibody is preferably labeled with a group which can be observed with a chromophoric substrate, an enzyme, for example, or a fluorescent or radioactive group, and the reaction between antibody and fragment is observed by measuring this label.

In preferred embodiments of the invention, a sample containing fragments of IgA1 is contacted first with a substance capable of reacting specifically with the Fc portion of IgA1. The substance may be, for example, a monoclonal antibody capable of binding specifically to the Fc portion of IgA1, or may be the IgA binding protein reported in copending application Ser. No. 446,317. Most preferably, this substance is immobilized on a solid support, paper, for example, or on a well in a plate. In these embodiments, the sample is first contacted with the immobilized substance which binds the Fc portion of both the fragment and also any unreacted, intact IgA1. The surface is then contacted with antibody capable of reacting only with the neo-epitope on the hydrolyzed fragment of IgA1. The antibody binds only to the fragment and is measured by a suitable label.

Measurement of fragments of IgA1 produced by IgAP is useful in assay of IgA1, or IgAP, and in detecting species which produce IgAP.

In certain embodiments of the present invention, immunoassay of fragments is used to determine IgA1. In these embodiments, a sample containing IgA1 is contacted with IgAP along with suitable buffers and ionic salts to provide conditions suitable for reaction between IgA1 and IgAP. Fragments having neo-epitopes produced by the IgAP will be formed and measured by immunoassay with antibody that recognizes specifically these neo-epitopes.

Samples which may be assayed for IgA1 include extracts from human membranes, human sera and other biological sources. Those monoclonal antibodies which belong to the IgA1 sub-class may also be assayed by the present method. This embodiment is of use, for example, in distinguishing between two classes of antibody in a sample or in a diagnostic procedure involving more than one class of monoclonal antibody. The method may also be used to test the purity of IgA2 which has been separated from IgA containing both IgA1 and IgA2. The presence of fragments in IgA after treatment with IgAP indicates IgA1.

In other embodiments, immunoassay of fragments is used to determine IgAP. In these embodiments, a sample containing IgAP is contacted with IgA1 under conditions suitable for reaction. The fragments produced are measured by immunoassay of the present invention.

The method of the present invention is especially useful in determining bacteria which produce IgAP. A sample containing the bacteria is contacted with substrate IgA1 and then assayed for fragments produced by the IgAP. The bacteria may be in culture or may be in a bacterial sample from an individual. Pathogenic bacteria which may be measured include Neisseria and Haemophilae. The assay is useful for diagnosis of diseases caused by the bacteria since IgAP is a marker for these bacteria.

The method of the present invention is especially useful in distinguishing between bacteria in a sample when more than one kind of bacteria which secrete IgAP is present. In these embodiments, fragments produced by action of IgAP on IgA1 are assayed with antibody which reacts specifically with neo-epitope on the fragments but which do not react with intact IgA1. The antibody has the additional property of being able to react with the fragment produced by IgAP from one bacteria but not with the fragment produced by IgAP from the other bacteria. This embodiment is especially useful in distinguishing *N. meningitides* from *N. gonorrhea.* These two bacteria often occur together in throat or rectal samples and the *N. meningitides* may cause no symptoms at these sites. A test for *N. gon.* in the presence of *N. men.* is therefore a useful diagnostic method. In the present invention, a sample from an individual, a throat swab, for example, is contacted with IgA1 and suitable buffers and ionic salts. The fragments thus produced are identified with antibody which reacts with fragments produced by gonorrheal IgAP and with antibody which reacts with fragments produced by meningeal IgAP.

When the fragments produced by the particular bacterial IgAP are thus defined, the bacteria are identified.

In other embodiments where IgA1 reacts with IgAP, in vivo extracts from membranes are assayed directly for fragments of IgA1 without any in vitro reaction with IgAP.

The method of the present invention is especially useful in the primary diagnosis of gonorrhea. It has been observed that extracts of uro-genital membranes contain fragments of IgA1. Vaginal swabs, for example, or urethral extract exhibits these fragments. Since the level of secretion of IgA1 rises upon infection, the amount of IgA1 present is significant and the fragments of IgA1 produced by IgAP from *N. gon.* may be measured by the immunoassay method of the present invention.

The present invention also provides reagent for detecting fragments of IgA1 produced by the reaction of IgAP and IgA1 comprising antibody which is capable of reacting with neo-epitope on the fragments which are not present on intact IgA1. The antibody, however, is incapable of reacting with intact IgA1 or epitopes on the fragments common to IgA1 and the fragments. Preferably, the reagent is monoclonal antibody produced by immunization of a host animal, a BALB/c mouse, for example, with fragments produced by the reaction of IgAP on IgA1. Monoclonal antibodies thus produced may be screened against IgA1 and the fragments. Those monoclonal antibodies which react with the fragments but not the intact IgA1 may be used as reagent in the present invention. The reagent may be used to detect bacteria which produce IgAP in a sample by contacting the sample with IgA1 and measuring the fragments produced with the reagent. A reagent for diagnosis of gonorrhea is provided comprising antibody which reacts specifically with the fragments produced by IgAP from *N. gon.*

A kit is provided for diagnosis of gonorrhea comprising the reagent which detects fragments produced by IgAP from *N. gon.* and ionic salts suitable for causing reaction between the fragments and the reagent. The kit may comprise, in addition, means for collection of extract from membranes which may support growth of *N. gon.*, urogenital membranes, throat or rectum, for example.

The following examples are intended to illustrate the present invention but are not intended to limit the scope of the invention thereby.

EXAMPLE 1

This example illustrates the primary diagnosis of gonorrhea in male or female patients.

(a) Sample Preparation

The infected area, vagina in the case of females and ureter in the case of males, is swabbed with an absorbent sterile dacron swab. The swab is immersed in 0.5 ml of a solution containing Tween 20 and a buffer at pH 7.2. The contents of the swab are repeatedly expressed into the buffer container and removed.

(b) Preparation of Specific Monoclonal Antibody

Monoclonal antibody is prepared by the Kohler and Millstein technique by immunizing a BALB/c mouse with fragments of IgA1 produced by enzymatic digestion with IgAP from *N. gonorrhea.* Hybridomas are formed by fusion of splenocytes from the mouse with SP-1 cells. Hybridoma cells are screened for those which produce monoclonal antibodies which bind to the fragment but do not bind to intact IgA1.

Selected monoclonal antibodies are lined to gold spheres by methods known in the art.

(c) Separation of IgA1 and Fragments from Sample

Monoclonal antibody for the Fc portion of IgA1 is immobilized on nitrocellulose paper by methods known in the art. A strip of paper is immersed in the sample and left to incubate for 15 minutes. The inert strip is removed from sample and rinsed with phosphate buffered saline (PBS).

(d) Detection of Fragment

The inert strip is placed in solution containing reagent from step (b) along with salts and buffers to cause reaction between fragments on the strip and reagent in solution. The strip is observed for color. Black strip indicates binding of labeled monoclonal antibody and is a positive indicator for gonorrhea. A control strip from non-infected sample does not bind monoclonal antibody and remains white.

What is claimed is:

1. Method for determining fragments of immunoglobulin A, sub-class 1 (IgA1) produced by enzymatic digestion of immunoglobulin A, sub-class 1 (IgA1) by immunoglobulin A protease (IgAP) comprising immunoassay of said fragments with antibody capable of reacting specifically with neo-epitope on said fragments, but incapable of reacting with intact IgA1, and relating the presence or absence of said neo-epitopes to the presence or absence of said fragments.

2. Method of claim 1, wherein said antibody is monoclonal antibody capable of reacting specifically with neo-epitope on fragments resulting from the enzymatic digestion of IgA1 by said IgAP, said neo-epitope not being present on intact IgA1.

3. Method of claim 1 wherein said immunoassay comprises competitive binding assay or sandwich immunoassay.

4. Method for detecting IgA1 in a sample comprising:
 (a) contacting said sample with IgAP under conditions suitable for enzymatic digestion to form fragments of IgA1; and
 (b) measuring said fragments by the method of claim 1.

5. Method for detecting the enzyme IgAP in a sample comprising:
 (a) contacting said sample with IgA1 under conditions suitable for reaction between IgAP and IgA1 to form fragments of IgA1; and
 (b) assaying said sample for said fragments by the method of claim 1.

6. Method for detecting bacteria which secrete the enzyme IgAP in a sample comprising assay of said sample for said enzyme by the method of claim 5.

7. Method of claim 6, wherein said bacteria are from the genus Neisseria, Haemophilus or Streptococcus.

8. Method of claim 6, wherein said sample is cultured prior to assay for said enzyme.

9. Method of diagnosis of gonorrhea in an individual comprising immunoassay of a sample from said individual for fragments produced in vivo by the reaction of IgAP from *Neisseria gonorrhea* with IgA1 by the method of claim 1.

10. Method of claim 9, wherein said specimen is extract of urogenital membrane.

11. Method of diagnosis of gonorrhea in an individual comprising:
 (a) contacting a sample from said individual with:

(i) a substance capable of binding specifically to the Fc portion of IgA1 under conditions suitable for binding between said IgA1 and said substance; and (ii) an antibody capable of reacting specifically with a neo-epitope on the Fc fragment of IgA1 resulting from the reaction of IgAP from *Neisseria gonorrhea* in vivo with IgA1 under conditions suitable for binding between said antibody and said fragment, wherein one of said antibody or said substance is immobilized on an inert surface and the other of said antibody or said substance is labeled with a detectable group;

(b) removing said fragment with bound substance and bound antibody from sample; and (c) measuring said detectable group that is bound to said surface or that is unbound in the sample; and (d) relating said measurement to the presence or absence of *Neisseria gonorrhea*.

12. Reagent for assay of fragments of IgA1 resulting from the enzymatic digestion of IgA1 and IgAP comprising antibody capable of reacting specifically with a neo-epitope on said fragments but incapable of reacting with intact IgA1.

13. Reagent of claim 12 wherein said antibody is a monoclonal antibody.

14. Reagent for detection of IgA1, comprising antibody of claim 12.

15. Reagent for detection of IgAP, comprising antibody of claim 12.

16. Reagent for assay of bacteria which produce IgAP comprising antibody capable of reacting specifically with neo-epitopes on fragments produced by reaction of IgA1 with IgAP from said bacteria but incapable of reacting with intact IgA1.

17. Reagent for diagnosis of gonorrhea comprising antibody of claim 12, said antibody being specific for neo-epitope on fragments produced by digestion of IgA1 with IgAP from *Neisseria gonorrhea*.

18. Kit for diagnosis of gonorrhea comprising reagent of claim 17, said reagent being either;
 (a) immobilized on an inert surface; or
 (b) labeled with a group capable of being observed.

19. Kit of claim 18, comprising, in addition, means for collection of extract from membrane suspected of supporting growth of *Neisseria gonorrhea*.

20. Method for distinguishing between bacteria which secrete IgAP comprising:

(a) contacting said bacteria with IgA1 under conditions suitable for reaction between IgAP from said bacteria and IgA1 to form fragments having neo-epitope characterized by having been produced by IgAP from a particular bacterial source, said neo-epitope not being present on intact IgA1 and also not being present on IgA1 fragments produced by the reaction of IgA1 with bacteria other than from said particular bacterial source;

(b) immunoassaying said fragments with antibody capable of reacting specifically with said neo-epitope but incapable of reacting with intact IgA1; and (c) relating the presence of said neo-epitopes to the presence of said particular bacterial source.

21. Method for determining fragments of immunoglobulin A, sub-class 1 (IgA1) produced by enzymatic digestion of said IgA1 by immunoglobulin A protease (IgAP) comprising:

(a) contacting said fragments with antibody capable of reaction specifically with neo-epitope produced by said enzymatic digestion, but incapable of reacting with intact IgA1, under conditions suitable for causing said antibody to become bound to said fragments, said antibody being labeled with a group capable of being observed;

(b) causing bound antibody to be separated from unbound antibody;

(c) observing label on that portion of said labeled antibody bound to said fragments or on that portion remaining unbound; and (d) relating said observation to the presence or absence of said fragments.

22. The kit of claim 18 comprising in addition means for maintaining conditions suitable for causing reaction between said reagent and fragments of IgA1 produced by reaction of IgA1 with IgAP from *Neisseria gonorrhea*.

23. Method of claim 20 wherein said bacteria being distinguished are *Neisseria gonorrhea* and *Neisseria meningitidis*, said neo-epitope produced by IgAP from *Neisseria gonorrhea* is characterized by having been produced by IgAP from *Neisseria gonorrhea* and not produced by IgAP from *Neisseria meninigitidis* and said neo-epitope produced by IgAP from *Neisseria meningitidis* is characterized by having been produced by IgAP from *Neisseria meningitidis* and not produced by IgAP from *Neisseria gonorrhea*.

* * * * *